United States Patent [19]

Panoz

[11] Patent Number: 4,822,617
[45] Date of Patent: Apr. 18, 1989

[54] DRUG DELIVERY DEVICE
[75] Inventor: Donald E. Panoz, Athlone, Ireland
[73] Assignee: Elan Corporation P.L.C., Athlone, Ireland
[21] Appl. No.: 37,108
[22] Filed: Apr. 10, 1987

Related U.S. Application Data

[63] Continuation of Ser. No. 827,190, Feb. 6, 1986, abandoned, which is a continuation of Ser. No. 568,693, Jan. 6, 1984, abandoned.

[30] Foreign Application Priority Data

Jan. 18, 1983 [IE] Ireland .................................. 94/83

[51] Int. Cl.4 ............................................. A61F 13/02
[52] U.S. Cl. ...................................... 424/449; 604/304
[58] Field of Search ................ 604/896, 897, 304–309; 424/447–449

[56] References Cited

U.S. PATENT DOCUMENTS

| 2,561,071 | 7/1951 | Prisk | 604/896 |
|---|---|---|---|
| 3,734,097 | 5/1973 | Zaffaroni | 604/304 |
| 3,742,951 | 7/1973 | Zaffaroni | 604/897 |
| 3,782,377 | 1/1974 | Rychlik | 604/307 |
| 3,814,095 | 6/1974 | Lubens | 604/307 |
| 3,910,284 | 10/1975 | Orentreich | 128/355 |
| 3,964,482 | 6/1976 | Gerstel et al. | 604/896 |
| 3,996,934 | 12/1976 | Zaffaroni | 604/897 |
| 4,031,894 | 6/1977 | Urquhart | 604/897 |
| 4,341,208 | 7/1982 | Gordon | 604/897 |
| 4,460,372 | 7/1984 | Campbell | 604/897 |
| 4,486,193 | 12/1984 | Shaw et al. | 604/897 |

FOREIGN PATENT DOCUMENTS

| 0013606 | 7/1980 | European Pat. Off. |
| 2314509 | 9/1973 | Fed. Rep. of Germany |
| 2902183 | 7/1980 | Fed. Rep. of Germany |
| 4138120 | 10/1979 | Japan |
| 57-77617 | 5/1982 | Japan |

Primary Examiner—C. Fred Rosenbaum
Assistant Examiner—Denise Whelton
Attorney, Agent, or Firm—Robert Hardy Falk; Harry J. Watson; Randy C. Brown

[57] ABSTRACT

A device for the unidirectional transdermal administration of a drug in an ointment, cream or jelly-like carrier comprising a laminar applicator adapted to receive a predetermined quantity of the drug on a skin-contacting surface thereof, the applicator including a drug-impervious lamina such as a layer of aluminum foil, overlying said skin-contacting surface, such that in use a unidirectional transfer of the drug from the carrier to the skin surface is ensured. The device is especially suitable for the transdermal administration of nitroglycerin, clonidine, methadone and scopolamine or any drug that is skin-permeable. The drug receiving surface may be embossed, pressed, or stamped to define one or more mini-recesses or receptacles for receiving the drug to be administered.

13 Claims, 2 Drawing Sheets

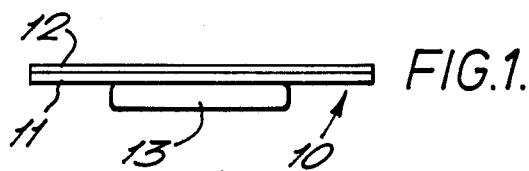
FIG.1.
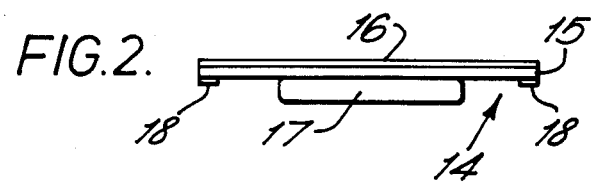
FIG.2.
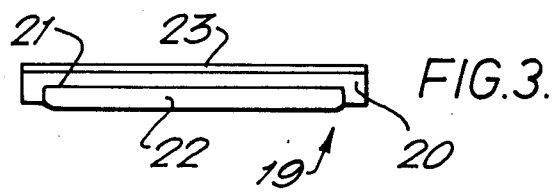
FIG.3.
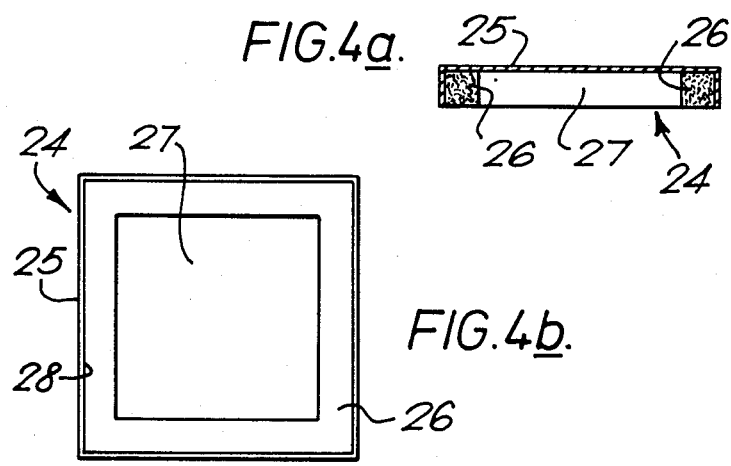
FIG.4a.
FIG.4b.

DRUG DELIVERY DEVICE

This application is a continuation of application Ser. No. 827,190, filed Feb. 6, 1986, which is a continuation of application Ser. No. 568,693, filed Jan. 6, 1984, now abandoned.

BACKGROUND OF THE INVENTION

1. Field of the Invention

This invention relates to a sustained release drug delivery device and, in particular, to a device for the transdermal or percutaneous delivery of drugs. The invention relates especially to a device for the systemic delivery of drugs by the transdermal route.

The advantages of administering certain drugs by the transdermal route are well known and include avoidance of drug deactivation by digestive enzymes or first-pass hepatic metabolism. However, these advantages are also characteristic of drug administration by parenteral routes such as by intramuscular injection or i.v. infusions.

2. Description of the Prior Art

Transdermal delivery for systemic therapy has been recognized as feasible for some considerable period of time, on the basis of ointment preparations of nitroglycerin, anti-inflammatory agents and hormones. For example, topical nitroglycerin ointment has been used in the United States of America for angina prophylaxis since the 1950s.

Until relatively recently—circa 1980—only parenteral administration offered precise control over rate of drug entry into the bloodstream and then only when closely monitored.

A number of transdermal devices have now been developed and consist essentially of transdermal or skin patches. Certain of these transdermal devices include a rate-controlling membrane between a drug reservoir and the skin surface. The rate-controlling membrane limits the amount of drug delivered per unit area of skin surface in a manner such that the device and not the skin is dominant in controlling the rate of drug input to the skin surface and hence to the systemic circulation.

A number of transdermal nitroglycerin patches are now on the U.S. market and are indicated for the prevention and treatment of angina pectoris due to coronary artery diseases. Although there are differences in composition, mechanism of drug delivery and appearance among the currently available transdermal nitroglycerin device all appear to be functionally similar. Examples of transdermal nitroglycerin patches are those marketed by Ciba Pharmaceutical Company under the trademark TRANSDERM-NITRO and manufactured by Key Pharmaceuticals, Inc under the trademark Nitro-Dur.

It is expected that these transdermal devices will largely replace nitroglycerin ointment in prophylactic angina therapy, since the ointment can be messy and needs to be applied several times a day because it retains its effectiveness for only 4–8 hours. Accordingly, patient acceptance and compliance can be a problem with such therapy.

It will be appreciated, however, that with transdermal therapy it is ultimately the inherent permeability of the skin that determines skin absorption of a drug and hence its delivery into the systemic circulation.

It has been established that the molecular permeability of skin is a passive rather than a biologically active property and that the stratum corneum, in particular the interstitial lipid phase thereof, is the principal barrier to drug permeation. It has been shown by Elias, P. M. et al (c.f., Clinical Research Vol. 30 No. 1, 1982) that regional differences in skin permeability may be related to regional differences in specific lipid content of the epidermis.

All of the currently available transdermal or skin patches discussed above are secured to the skin by a layer of adhesive extending over the skin-contacting surface of the device. In the case of the above-mentioned nitroglycerin patches it is recommended that the patches be applied to a hairless region of the body such as the upper arm or chest. Shaving of a suitable area for application of the patch may be necessary. However, shaving may cause local skin irritation and change the permeability characteristics of the products. All the currently available transdermal products are approved for once-daily administration and it is recommended that one alternates application sites daily.

It will be appreciated that the repeated application and removal of such patches, involving a securing layer of adhesive, can result in skin irritation and sensitization with prolonged use. It will also be appreciated that a certain amount of pain and discomfort is experienced on removing the patches.

It will also be appreciated that the currently available transdermal devices are of a relatively complicated design, including as they do various rate-controlling delivery systems, and consequently are relatively costly.

Conventionally, nitroglycerin ointment or cream has been applied to a given area of the body such as the chest by squeezing a predetermined amount of ointment onto a piece of paper and applying the paper with the ointment loaded thereon to the body, the ointment providing the necessary adhesion of the paper to the body.

Generally, the paper applicator used consists of a ruled piece of waxed paper. When one wishes to apply a given quantity of active ingredient carried by the ointment one squeezes a given amount of the ointment, for example one inch, from a tube onto the ruled piece of waxed paper in accordance with the drug manufactures' package directions.

The paper in addition to serving as an applicator for the ointment, provides a protective layer over the ointment and prevents the ointment from coming into contact with the hands of a nurse or other person applying the ointment to the skin.

However, the paper does not ensure a unidirectional transfer of the nitroglycerin or other active ingredient to the skin. Nitroglycerin for example will migrate through the paper and escape into the atmosphere. Effectively, the nitroglycerin can leave the site of application in any direction and, accordingly, the potential effect of topical nitroglycerin therapy is correspondingly reduced.

It is an object of the present invention to provide a transdermal device which incorporates a drug suitable for transdermal administration in an ointment carrier and which ensures a unidirectional transfer of the drug to the skin.

SUMMARY OF THE INVENTION

Accordingly, the invention provides a device for the unidirectional transdermal administration of a drug in an ointment, cream or jelly-like carrier, which device comprises a laminar applicator adapted to receive a predetermined quantity of the drug on one of its two major surfaces and having at least one major surface composed of a material impervious to said drug such that in use a unidirectional transfer of the drug from the carrier to the skin surface is ensured.

Hereinafter in this Specification the expression ointment carrier also embraces cream or jelly-like carriers.

The device according to the invention is suitable for the administration of any drug which when applied to an area of intact skin acceptable to physician and patient can elicit an adequate systemic therapeutic effect. The device according to the invention has general applicability for achieving a constant therapeutic effect with any drug that is permeable to the skin and which experiences a high degree of liver metabolism. The device is particularly applicable to potent drugs with narrow therapeutic indices, short half-lives or gastrointestinal problems.

The device is especially suitable for the transdermal administration of effective doses of nitroglycerin, isosorbide dinitrate or isosorbide monostearate of sustained duration in the prophylactic treatment of angina. The device is also especially suitable for the transdermal administration of Clonidine for the treatment of hypertension, Methadone for the treatment of drug abuse and Scopolamine for the treatment of motion sickness.

The drug may be carried by the ointment in its pure state or in admixture with one or more agents which facilitate its association with said ointment or its release to the skin surface.

The ointment may be any pharmaceutically or veterinarily acceptable ointment. An especially preferred ointment is one comprising a lanolin-petrolatum base.

The laminar applicator has preferably a bilaminar structure comprising a drug receiving lamina and an intimately associated drug impervious lamina.

The drug receiving lamina may consist of paper, cardboard, foam or suitable plastics material which is adapted to receive a predetermined amount of the drug to be administered.

The foam may be any suitable plastics or rubber foam. A particularly suitable foam material is expanded, cellular polystyrene sold under the Trade Mark STYROFOAM.

The skin contacting surface of the applicator must, of course, be inert and hypo-allergenic.

The drug impervious lamina is composed of any suitable drug impervious material such as aluminum or a sythetic resin polymer, such as tetrafluoroethylene fluorocarbon polymer (TFE) or fluorinated ethylene-propylene (FEP). An especially preferred drug impervious material for drugs such as nitroglycerin is aluminum foil.

The applicator suitably comprises a paper-aluminum bilayer 1 mm. in thickness.

However, it will be appreciated that the device could comprise a single layer of a drug impervious material.

The applicator will normally have a thickness less than 5.0 mm. and especially less than 3.0 mm.

The applicator may be of any suitable shape but is preferably round, square or oblong.

One suitable form of nitroglycerin transdermal device according to the invention is one wherein the laminar applicator is loaded with a predetermined amount of an ointment which contains 2% nitroglycerin and lactose in a special absorptive lanolin and white petrolatum base formulated to provide a controlled release of the active ingredient. Such an ointment is sold under the trademark NITRO-BID. Each inch of ointment as squeezed from the tube contains 15 mg. of nitroglycerin.

The surface area of the device according to the invention is suitably in the range of 6.25–25 cm.$^2$.

However, it will be appreciated that the surface area of the device will be determined by a number of factors such as severity of condition and required therapeutic effect.

It will be appreciated that the greater the surface area of the device the greater the skin absorption of the active ingredient.

The drug receiving lamina may be embossed, pressed or stamped to define one or more mini-recesses or receptacles for receiving the ointment. The or each recess may also be defined by cut-outs in a strip of flexible foam. Furthermore, the or each recess may be defined by foam strips suitably affixed to a lamina as hereinabove defined. The or each recess may be of any suitable shape.

In use, the ointment serves to secure the device to the skin. However, the drug receiving lamina may have a peripheral strip of adhesive for improving adhesion of the device to the body, if desired. The or each recess or receptacle would suitably have a depth of 0.5 mm–7.5 mm.

Studies have shown that the most efficient transdermal absorption of nitroglycerin occurs through the forehead. However, absorption through the forehead also results in the highest incidence of side effects such as headache and burning at the application site (c.f. Hansen et al Heart & Lung July–August 1979 Vol. 8 No. 4 at page 716).

The favoured application site consistent with good absorption and minimal side effects is the chest. However, further studies on the percutaneous absorption of nitroglycerin in rhesus monkeys by Noonan and Webster have shown that absorption through the chest, arm and thigh for equivalent doses applied to 2-cm2 areas did not result in statistically different absorption values (Journal of Pharmaceutical Sciences Vol. 69 No. 3, March 1980).

It will be appreciated that a patient may concurrently wear more than one device according to the invention to achieve an adequate or desired therapeutic effect.

The invention also provides a method of administering a drug transdermally to a patient which comprises applying a device as hereinabove defined to the desired site of drug administration.

DESCRIPTION OF THE DRAWINGS

The invention will be understood from the following description of embodiments thereof given by way of example only with reference to the accompanying drawings in which:

FIG. 1 is a schematic representation in front elevation of one embodiment of a device according to the invention;

FIG. 2 is a schematic representation in front elevation of a second embodiment of a device according to the invention;

FIG. 3 is a schematic representation in front elevation of a third embodiment of a device according to the invention;

FIG. 4a is a front elevation of a fourth embodiment of a device according to the invention;

FIG. 4b is a plan view of the device of FIG. 4a; and

DETAILED DESCRIPTION

Figure 5:
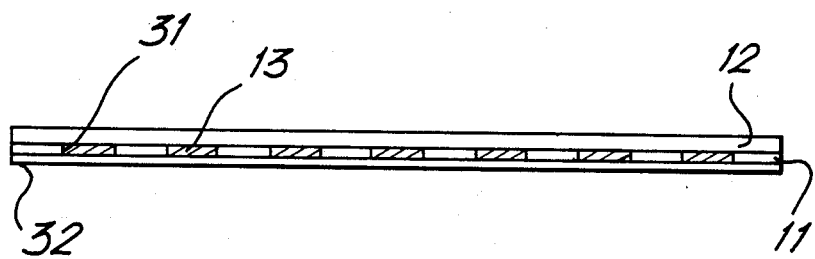
FIG. 5 is a schematic representation in front elevation of an alternative form of the embodiment shown in FIG. 1.

Referring to FIG. 1 of the drawings there is illustrated a transdermal device according to the invention indicated generally at 10. The device 10 comprises a square bilaminar application consisting of a layer of waxed ruled paper 11 having a backing layer of aluminum foil 12 bonded thereto. The paper 11 has loaded thereon one inch of an ointment 13 which contains 2% nitroglycerin and lactose in a special absorptive lanolin and white petrolatum base formulated to provide a controlled release of the active ingredient. Such an ointment is sold under the trademark NITRO-BID as is herewith referred to as NITRO-BID Ointment. One inch of said ointment corresponds to 15 mg. of nitroglycerin.

Referring to FIG. 2 of the drawing there is illustrated an alternative transdermal device according to the invention indicated generally at 14 and which comprises a bilaminar applicator consisting of a layer of plastics coated ruled cardboard 15 having a backing layer of aluminum foil 16 bonded thereto. The cardboard 15 has loaded thereon one inch of NITRO-BID ointment 17 corresponding to 15 mg. of niroglycerin. The cardboard 15 has a peripheral thin strip 18 of a suitable adhesive which provides greater adhesion of the device 14 to the skin in use, but which permits the device to be readily removed from the skin when desired.

Referring to FIG. 3 of the drawings there is illustrated a further transdermal device according to the invention indicated generally at 19 and which consists of a layer of plastics coated expanded synthetic resinous material 20, such as that sold under the trademark STYROFOAM, having a pressed recess 21 for receiving a predetermined amount of a drug-carrying ointment 22. The layer 20 is backed by a layer of aluminum foil 23 which is bonded thereto in conventional manner.

Referring to FIGS. 4a and 4b of the drawings there is illustrated a further transdermal device according to the invention, indicated generally at 24, and which device consists of a lamina of aluminum foil 25 (4 cm²) having a peripheral edge strip 26 of flexible foam affixed thereto so as to define a reservoir 27 internally of the edge strip 26. In use, a predetermined amount of nitroglycerin ointment is received in the reservoir 27. The aluminum foil 25 also embraces and covers external walls 28 of the edge strip 26.

The presence of the flexible foam strip 26 obviates what is known in the art as the "tunnelling effect" by ensuring good contact between the device 24 and the skin in use and thereby preventing leakage of air to the application site on the body.

With the device according to the invention it is possible to achieve a once daily application of nitroglycerin ointment as opposed to the eight-hourly application of nitroglycerin ointment as currently practiced.

The device according to the invention will generally be loaded with the drug to be administered at the time of administration. However, it will be appreciated that a device according to the invention which is provided with one or more recesses could be pre-loaded with the ointment and sold as a unit. FIG. 5 shows an alternative form of the embodiment of FIG. 1. The drug-receiving lamina 11 is embossed, pressed or stamped to define a plurality of mini-recesses or receptacles 31 which are charged with the ointment 13. The ointment containing recesses 31 are covered with a layer of drug impervious and preferably ointment repellent material 32 which is peeled off prior to use.

The devices according to the invention are considerably more effective than conventional topical/transdermal medicinal ointment therapy since they result in greater drug absorption by the skin due to the unidirectional transfer of the drug from the ointment.

Topical nitroglycerin ointment has not hitherto been useful for acute attacks of angina because of its slow onset profile.

However, it is envisaged that nitroglycerin carrying devices according to the invention will be useful even for acute attacks of angina due to their greater effectiveness resulting from the unidirectional transfer of nitroglycerin.

The devices according to the invention have a longer duration of activity compared with conventional topical nitroglycerin ointment therapy because they result in substantially all of the active ingredient in the ointment being transferred to the skin and thence to the systemic circulation.

I claim:

1. A bilaminarly-structured device for the transdermal administration of a drug to a patient comprising:
   a drug-receiving and retaining means accessible to a user of the device, said means being provided on a first laminar member having a first face and a second face, said first laminar member having on said first face a predetermined amount of a drug in an ointment, cream or jelly-like carrier, said ointment, cream or jelly-like carrier, which includes said drug, being contained in a recess and projecting outwardly from said recess beyond the first face so that said drug in said ointment, cream or jelly-like carrier can be placed in direct contact with the user's skin and the carrier serves to secure the device to the skin; and
   means effectively restricting the dispersion of the drug from said first laminar member to the direction of the skin whereby an effective amount of said drug is delivered to the user's skin, in use, said restricting means comprising a second and drug impervious, laminar member affixed to said first laminar member to form a bi-laminar structure which covers said second face of said first laminar member and said restricting means further including a peripheral wall on said first laminar member defining said recess.

2. A device according to claim 1, wherein the first, drug-receiving, laminar member consists of paper, cardboard, foam or plastics material.

3. A device according to claim 1, wherein the second, drug-impervious, laminar member is composed of aluminum.

4. A device according to claim 3, wherein the second, drug-impervious, laminar member is composed of aluminum foil.

5. A device according to claim 1, wherein the second drug-impervious, laminar member is composed of a tetrafluoroethylene fluorocarbon polymer of fluorinated ethylene-propylene.

6. A device according to claim 1, wherein the first and second laminar members comprise a paper-aluminum foil bilayer of approximately 1 mm in thickness.

7. A device according to claim 1, having a surface area in the range 6.25–25 cm².

8. A device according to claim 1, wherein the first, drug-receiving, laminar is embossed, pressed or stamped to define one or more mini-recesses or receptacles for receiving the drug.

9. A bilaminarly-structured device for the transdermal administration of a drug to a patient comprising:
a drug-receiving and retaining means, said means being provided on a first laminar member having a first face and a second face, said first laminar member having on said first face a predetermined amount of a drug, in an ointment, cream or jelly-like carrier, said ointment, cream or jelly-like carrier, which includes said drug in admixture with one or more agents which facilitate association of the drug with said carrier and the release thereof to the skin surface being contained in a recess and projecting outwardly from said recess beyond the first face so that said drug in said ointment, cream or jelly-like carrier can be placed in direct contact with the skin surface of a user of the device and the carrier serves to secure the device to the skin; and
means effectively restricting the dispersion of the drug from said first laminar member except to the direction of the skin whereby an effective amount of said drug is delivered to the skin surface of a user of the device, said restricting means comprising a second, and drug-impervious, laminar member affixed to said first laminar member to form a bilaminar structure said restricting means covering said second face of said first laminar member and further including a peripheral wall on said first laminar member defining said recess;
wherein said carrier has an inherent tackiness and wherein said device in use adheres to the skin surface of said user of the device by virtue of said inherent tackiness of said carrier, thereby minimizing skin irritation caused by repeated application of said device and wherein the skin of said user of the device controls the rate of drug input to the systemic circulation of said user.

10. A device according to claim 9, wherein the carrier is an ointment having a lanolin-petrolatum base.

11. A device according to claim 9, wherein the drug is nitroglycerin, isosorbide dinitrate, isosorbide monostearate, clonidine, methadone or scopolamine.

12. A device according to claim 11, wherein the drug is nitroglycerin at a concentration of 2% by weight in a lanolin-white petrolatum base.

13. A method of administering a drug transdermally to a patient, which comprises applying a device as claimed in claim 9 to the desired site of drug administration.

* * * * *